US012746157B2

(12) United States Patent
Ruan et al.

(10) Patent No.: US 12,746,157 B2
(45) Date of Patent: Sep. 29, 2026

(54) CHEST SEAL

(71) Applicant: ROOSIN MEDICAL CO., LTD., Taizhou (CN)

(72) Inventors: Shaowei Ruan, Taizhou (CN); Dayong Chen, Taizhou (CN); Jiamian Chu, Taizhou (CN)

(73) Assignee: ROOSIN MEDICAL CO., LTD., Taizhou (CN)

(*) Notice: Subject to any disclaimer, the term of this patent is extended or adjusted under 35 U.S.C. 154(b) by 0 days.

(21) Appl. No.: 19/187,974

(22) Filed: Apr. 23, 2025

(65) Prior Publication Data

US 2025/0275873 A1 Sep. 4, 2025

(30) Foreign Application Priority Data

Feb. 21, 2025 (CN) ......................... 202510198074.9

(51) Int. Cl.

| | |
|---|---|
| ***A61F 13/02*** | (2024.01) |
| ***A61F 13/00*** | (2024.01) |
| ***A61F 13/0246*** | (2024.01) |

(52) U.S. Cl.

CPC ........ *A61F 13/0233* (2013.01); *A61F 13/023* (2013.01); *A61F 13/0253* (2013.01);

(Continued)

(58) Field of Classification Search

CPC .... A61F 13/023; A61F 13/0233; A61F 13/05; A61F 13/143; A61F 2013/00106;

(Continued)

(56) References Cited

U.S. PATENT DOCUMENTS

| | | | |
|---|---|---|---|
| 2013/0317405 | A1 | 11/2013 | Ha et al. |
| 2015/0320919 | A1 | 11/2015 | Bussett et al. |

(Continued)

FOREIGN PATENT DOCUMENTS

| | | | |
|---|---|---|---|
| CN | 2689944 | Y | 4/2005 |
| CN | 205215519 | U | 5/2016 |

(Continued)

OTHER PUBLICATIONS

Notice of Allowance of counterpart Chinese Patent Application No. 202510198074.9 issued on Aug. 25, 2025.

(Continued)

*Primary Examiner* — Keri J Nelson
*Assistant Examiner* — Seth R. Brown

(57) ABSTRACT

A chest seal is provided, including a release layer; an adhesive layer, a center of the adhesive layer being opened with an exhaust through hole; and a backing layer. The adhesive layer is arranged between the release layer and the backing layer; the backing layer includes a lower backing layer and a soft backing layer; the lower backing layer and the soft backing layer are staggered and form an overlapping area; the overlapping area includes a connection area and a non-connection area; and the lower backing layer is arranged above the adhesive layer and does not completely block the exhaust through hole. The chest seal can prevent external air from entering the chest cavity and discharge the effusion in the chest cavity when a penetrating wound is formed in the chest cavity through the structural design between the exhaust through hole, the lower backing layer, and the soft backing layer.

8 Claims, 15 Drawing Sheets

(52) U.S. Cl.
CPC ..................... *A61F 13/0263* (2013.01); *A61F 2013/00106* (2013.01); *A61F 2013/00536* (2013.01); *A61F 2013/00604* (2013.01); *A61F 2013/00676* (2013.01); *A61F 2013/00702* (2013.01); *A61F 2013/00859* (2013.01)

(58) Field of Classification Search
CPC .. A61F 2013/00114; A61F 2013/00246; A61F 2013/00251; A61F 2013/00268; A61F 13/0203; A61F 13/0253; A61F 13/0263; A61F 2013/00165; A61F 2013/00217; A61F 2013/00255; A61F 2013/00536; A61F 2013/00553; A61F 2013/00604; A61F 2013/00676; A61F 2013/00702; A61F 2013/00859
USPC ...................... 602/42–59; 604/540, 541, 543

See application file for complete search history.

(56) References Cited

U.S. PATENT DOCUMENTS

| | | | | |
|---|---|---|---|---|
| 2019/0298578 | A1* | 10/2019 | Shulman | A61F 13/0213 |
| 2022/0218533 | A1* | 7/2022 | Harder | B29C 65/18 |

FOREIGN PATENT DOCUMENTS

| | | | |
|---|---|---|---|
| CN | 107928879 | A | 4/2018 |
| CN | 111542289 | A | 8/2020 |
| CN | 213156978 | U | 5/2021 |
| CN | 215135544 | U | 12/2021 |
| CN | 219184532 | U | 6/2023 |
| CN | 221106234 | U | 6/2024 |

OTHER PUBLICATIONS

1st Office Action of counterpart Chinese Patent Application No. 202510198074.9 issued on Jul. 16, 2025.
First Search Report of counterpart Chinese Patent Application No. 202510198074.9 issued on Jul. 14, 2025.

* cited by examiner

CHEST SEAL

CROSS-REFERENCE TO RELATED APPLICATIONS

The present application claims the benefit of Chinese Patent Application No. 202510198074.9 filed on Feb. 21, 2025, the contents of which are incorporated herein by reference in their entirety.

TECHNICAL FIELD

The present disclosure relates to the technical field of chest seals, and in particular to a chest seal.

BACKGROUND

Open pneumothorax is caused by trauma that causes full-thickness damage to the chest wall tissue. During breathing, as the chest wall expands and the diaphragm contracts, negative pressure will be generated in the chest cavity, and air will enter the lungs through the upper respiratory tract and bronchi. When the chest wall retracts and the diaphragm relaxes, positive pressure is generated in the lungs to expel gas from the respiratory tract. When the chest cavity ruptures and the wound continues to open, air will enter the chest cavity from the wound and change the chest pressure. Air cannot enter the lungs, which eventually leads to pneumothorax and lung collapse. If the wound size exceeds the diameter of the trachea, the air entering the chest cavity will exceed the air volume entering the lungs, resulting in hypoxia.

The treatment for open chest injuries is to close the wound and prevent air from entering the chest cavity. At present, sterile dressings or cotton pads are generally used to overlap the wound, and then taped or bandaged to fix it, so that open pneumothorax becomes closed pneumothorax and the patient is then sent to a hospital for further treatment urgently. The current emergency treatment methods for open pneumothorax are cumbersome and unsatisfactory, which poses a hidden danger in the emergency treatment of such patients.

SUMMARY

In order to solve the problem that the emergency treatment method for open pneumothorax in the existing art is cumbersome to operate and results in unsatisfactory effect, the present disclosure provides a chest seal. The chest seal can prevent external air from entering the chest cavity and discharge the effusion in the chest cavity when a penetrating wound is formed in the chest cavity through the structural design between an exhaust through hole, a lower backing layer, and a soft backing layer.

The technical solution adopted by the present disclosure to solve its technical problems is as follows:

a chest seal, the chest seal including:

a release layer;

an adhesive layer, a center of the adhesive layer being opened with an exhaust through hole; and a backing layer. The adhesive layer is arranged between the release layer and the backing layer; the backing layer includes a lower backing layer and a soft backing layer; the lower backing layer and the soft backing layer are staggered and form an overlapping area; and the lower backing layer is arranged above the adhesive layer and does not completely block the exhaust through hole, a non-block area is formed between the lower backing layer and the exhaust through hole, and the soft backing layer completely covers the non-block area.

In some embodiments, the adhesive layer is consistent with the shape of the backing layer.

In some embodiments, the cross section of the non-block area is 1/50~4/5 of the cross section of the exhaust through hole.

In some embodiments, the lower backing layer includes an inner periphery and an outer periphery; the inner periphery is provided with at least one notch; the notch is arranged in the overlapping area; and the notch is connected to the exhaust through hole.

In some embodiments, the overlapping area includes a connection area and a non-connection area, and the non-connection area is located above the exhaust through hole.

In some embodiments, the connection area is at both ends of the overlapping area, and the area of the connection area is greater than 0.

In some embodiments, the notch is an arc-shaped notch whose edge coincides with an edge of the exhaust through hole.

In some embodiments, the soft backing layer is selected from at least one of polyethylene film, polyurethane film, and silicone rubber film.

In some embodiments, the release layer is selected from at least one of polyethylene (PE) release film, polyethylene terephthalate (PET) release film, oriented polypropylene (OPP) release film, composite release film, glassine release paper, coated release paper, and clay coated kraft (CCK) release paper.

In some embodiments, the adhesive layer is selected from at least one of silicone gel layer, hydrocolloid layer, and hydrogel layer.

The beneficial effects of the present disclosure are as follows:

The chest seal provided by the present disclosure utilizes the structural design between the exhaust through hole, the lower backing layer, and the soft backing layer to prevent external air from entering the chest cavity and discharge the effusion in the chest cavity when a penetrating wound is formed in the chest cavity. Moreover, by adjusting the size of the non-block area between the lower backing layer and the exhaust through hole, the drainage efficiency can be accurately controlled. In addition, the chest seal can change an open pneumothorax into a closed pneumothorax, which is simple and quick to operate. It is suitable for emergency treatment of open pneumothorax, reduces the patient's demand for medical resources, and thus saves medical costs to a certain extent.

BRIEF DESCRIPTION OF DRAWINGS

The present disclosure will be further described below with reference to figures and embodiments.

DISCLOSURE

Figure 1:
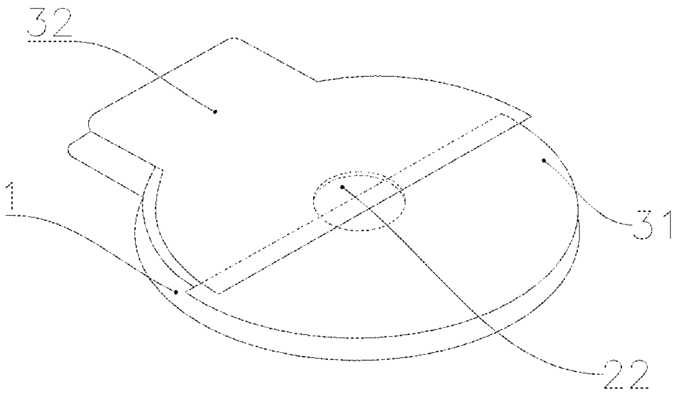
FIG. 1 is schematic diagram I of a structure of a chest seal according to the present disclosure.
Figure 2:
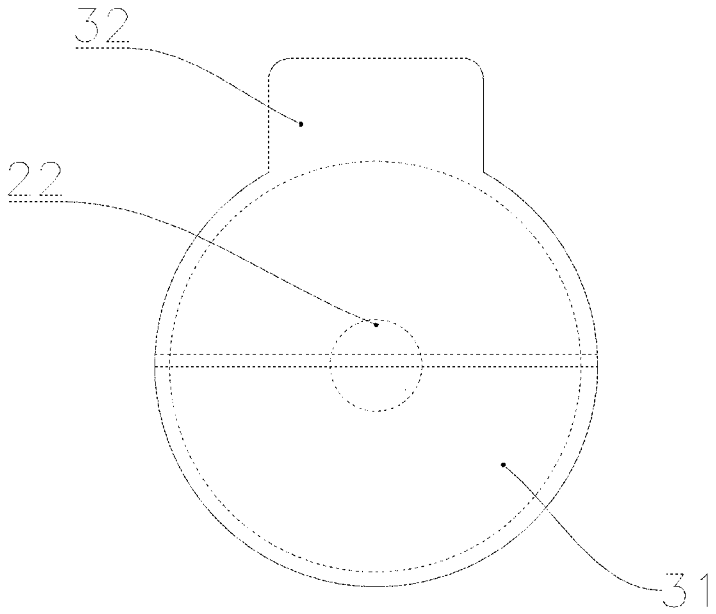
FIG. 2 is schematic diagram II of a structure of a chest seal according to the present disclosure.
Figure 3:
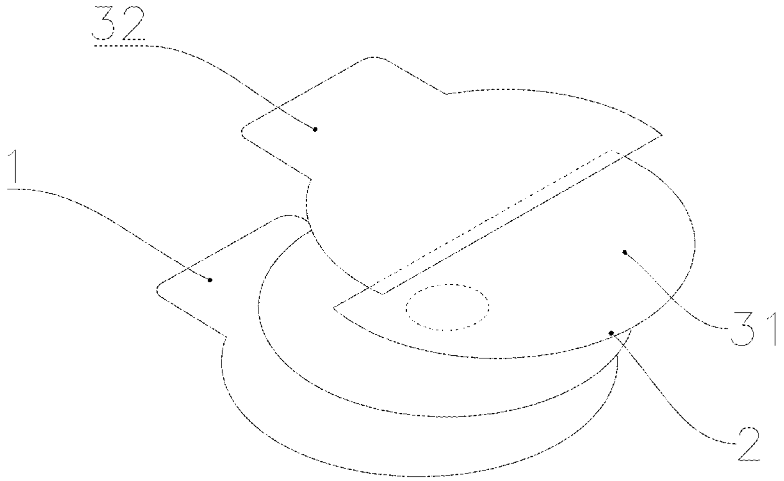
FIG. 3 is schematic diagram III of a structure of a chest seal according to the present disclosure.
Figure 4:
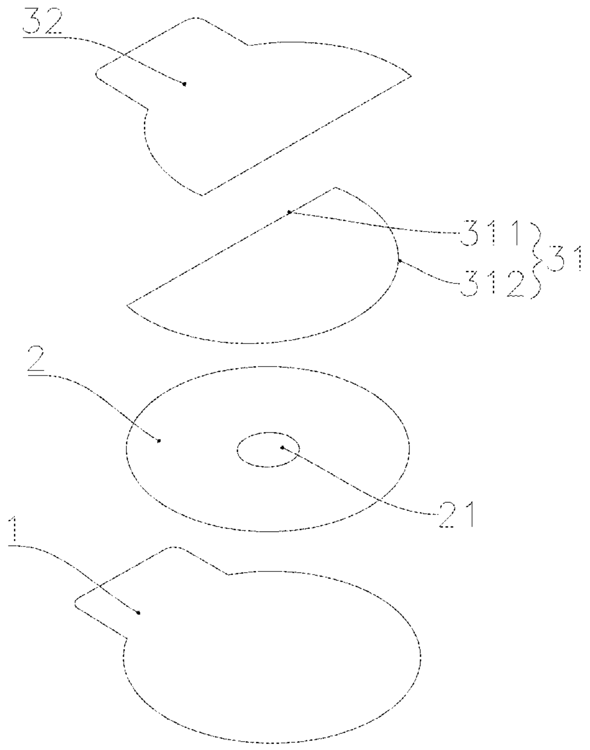
FIG. 4 is exploded schematic diagram I of a chest seal according to the present disclosure.
Figure 5:
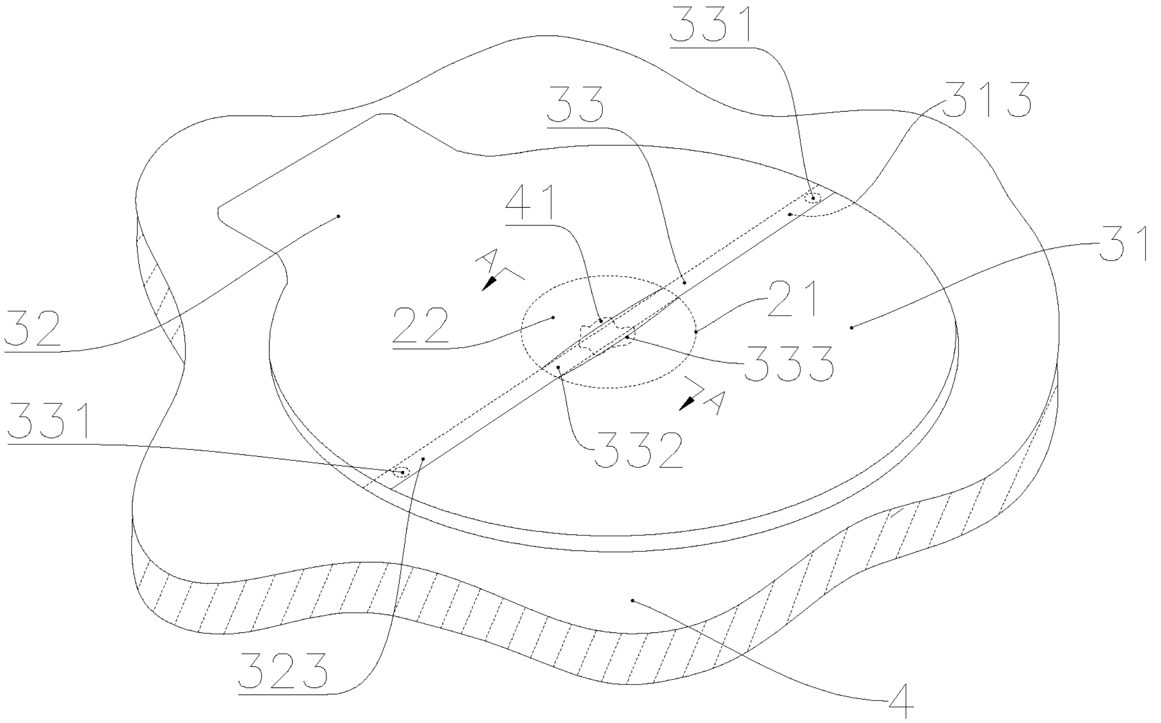
FIG. 5 is schematic diagram I illustrating use of a chest seal according to the present disclosure.
Figure 6:
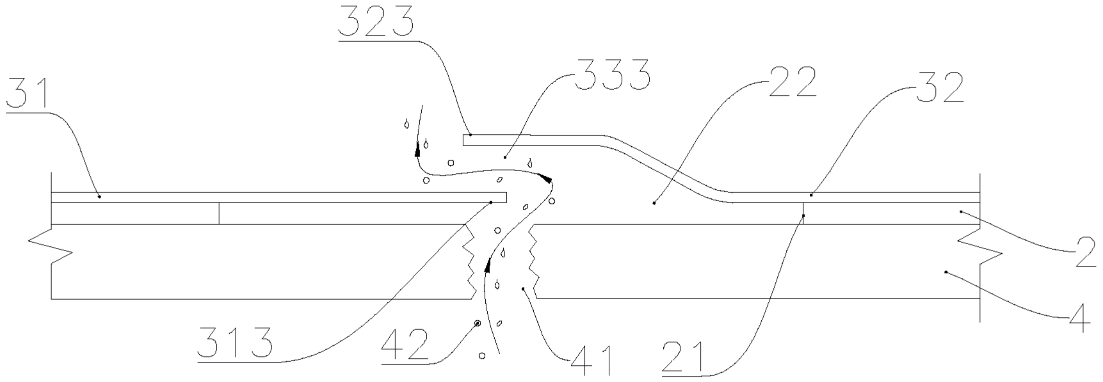
FIG. 6 is a cross-sectional view at A-A in FIG. 5.
Figure 7:
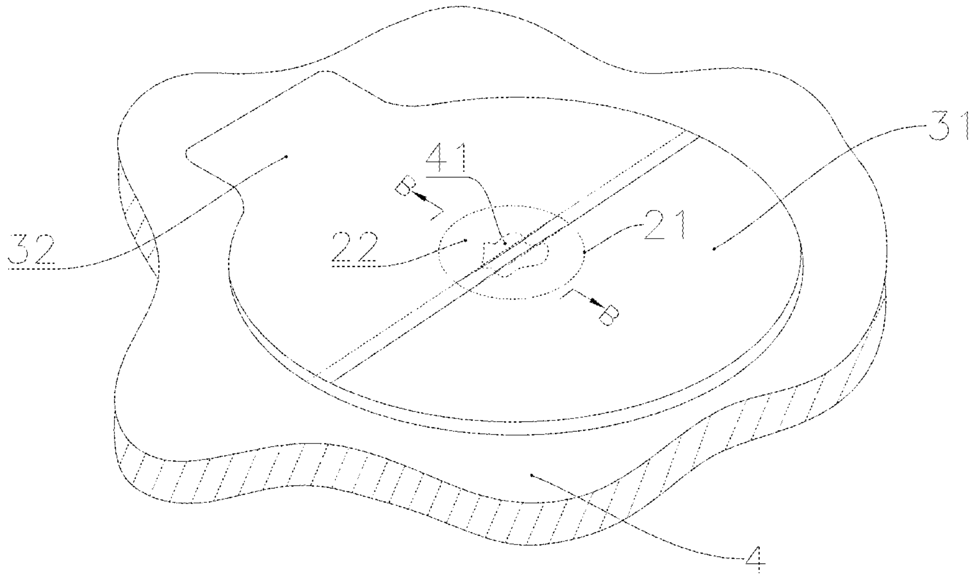
FIG. 7 is schematic diagram II illustrating use of a chest seal according to the present disclosure.
Figure 8:
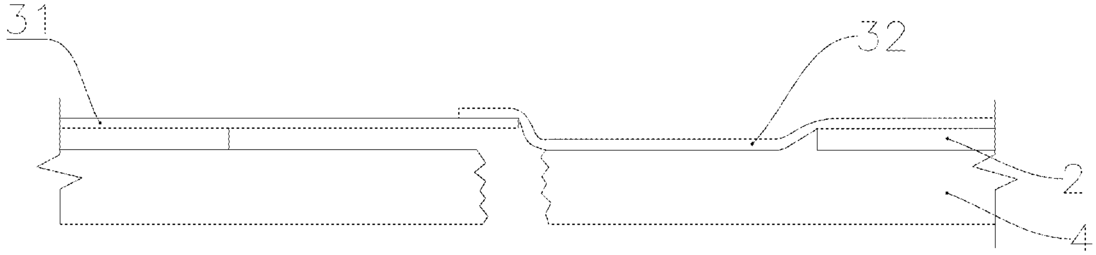
FIG. 8 is a cross-sectional view at B-B in FIG. 7.
Figure 9:
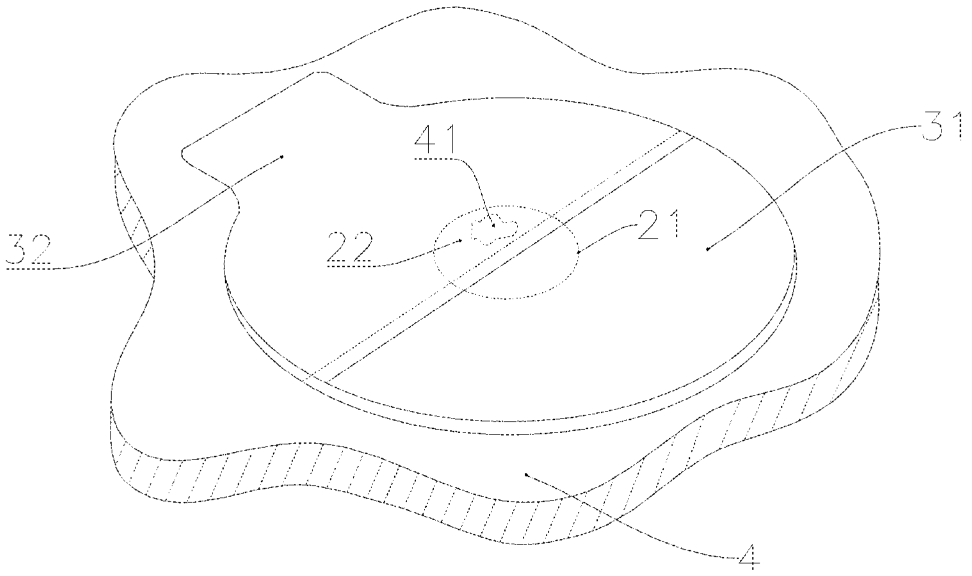
FIG. 9 is schematic diagram III illustrating use of a chest seal according to the present
Figure 10:
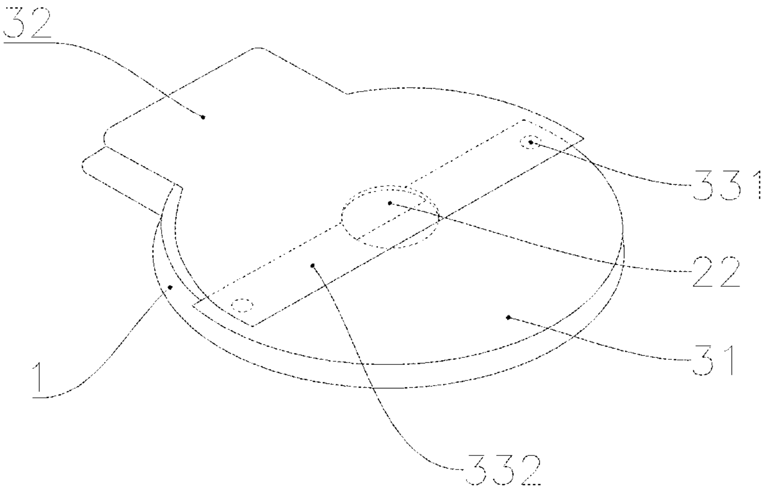

FIG. 10 is schematic diagram IV of a structure of a chest seal according to the present disclosure.

Figure 11:
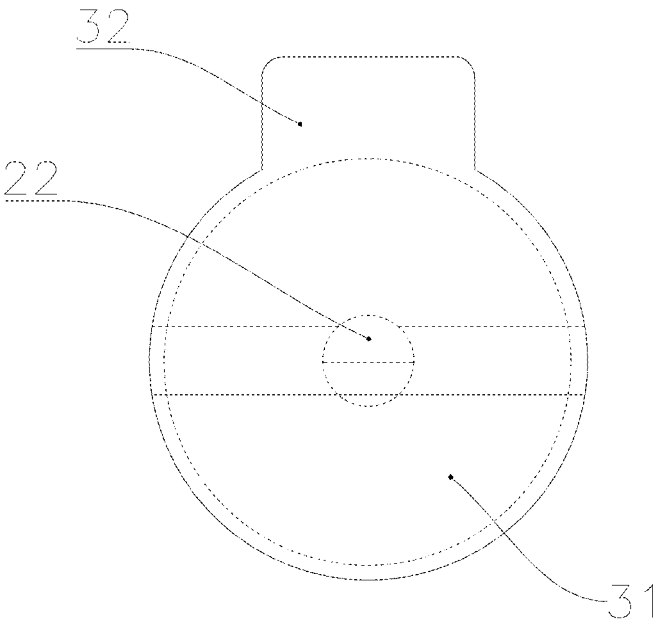

FIG. 11 is schematic diagram V of a structure of a chest seal according to the present disclosure.

Figure 12:
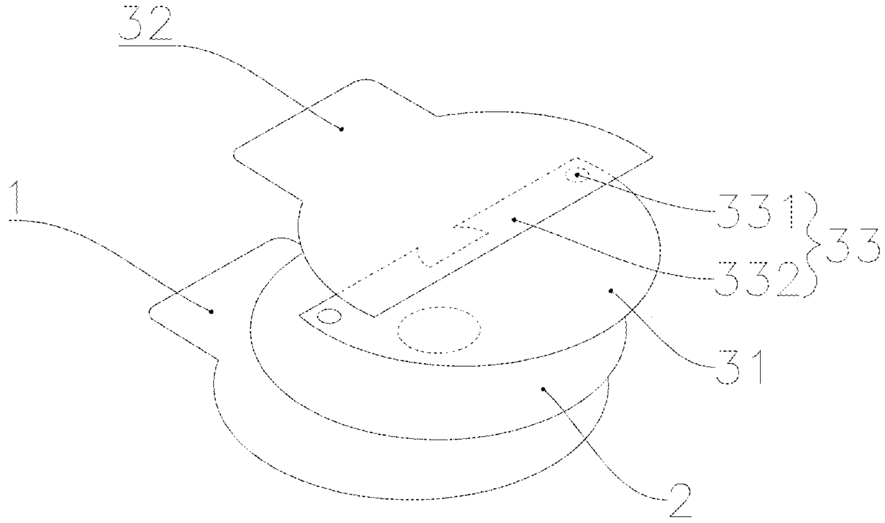

FIG. 12 is schematic diagram VI of a structure of a chest seal according to the present disclosure.

Figure 13:
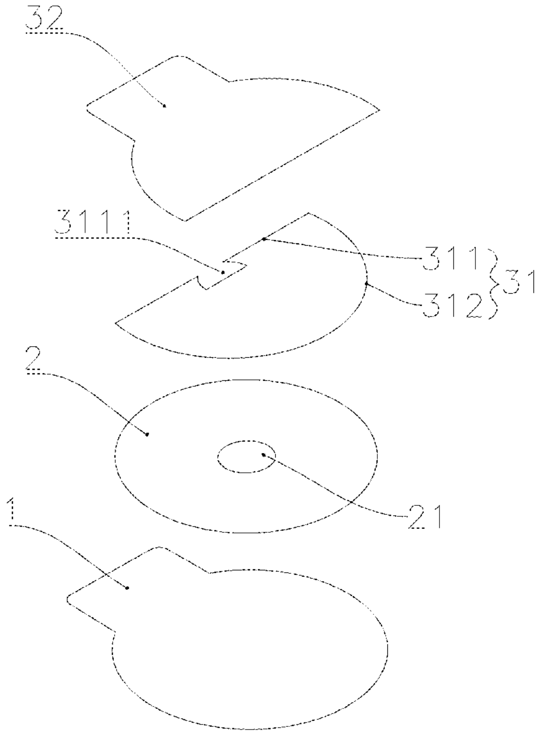

FIG. 13 is exploded schematic diagram II of a chest seal according to the present disclosure.

Figure 14:
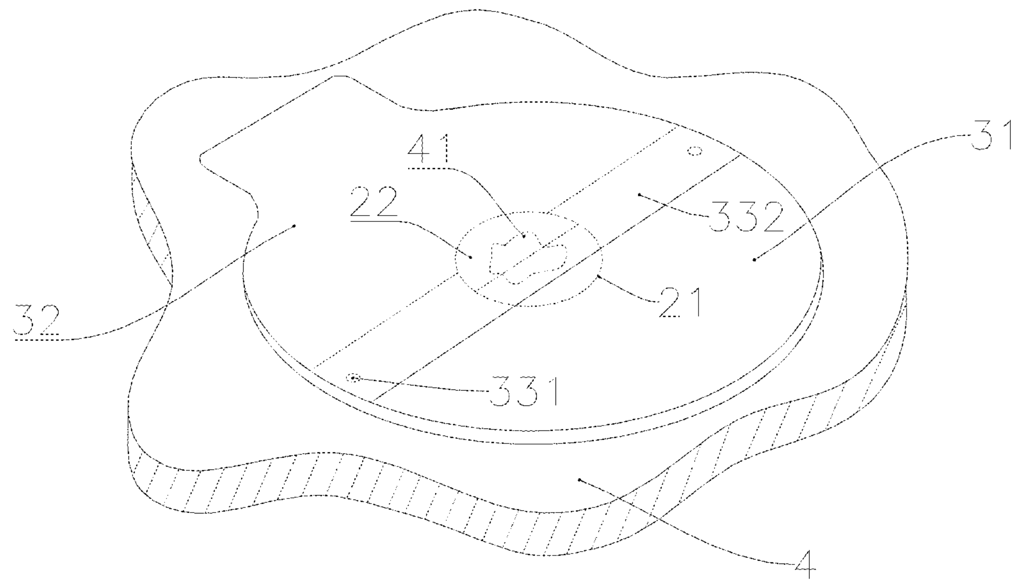

FIG. 14 is schematic diagram IV illustrating use of a chest seal according to the present disclosure.

Figure 15:
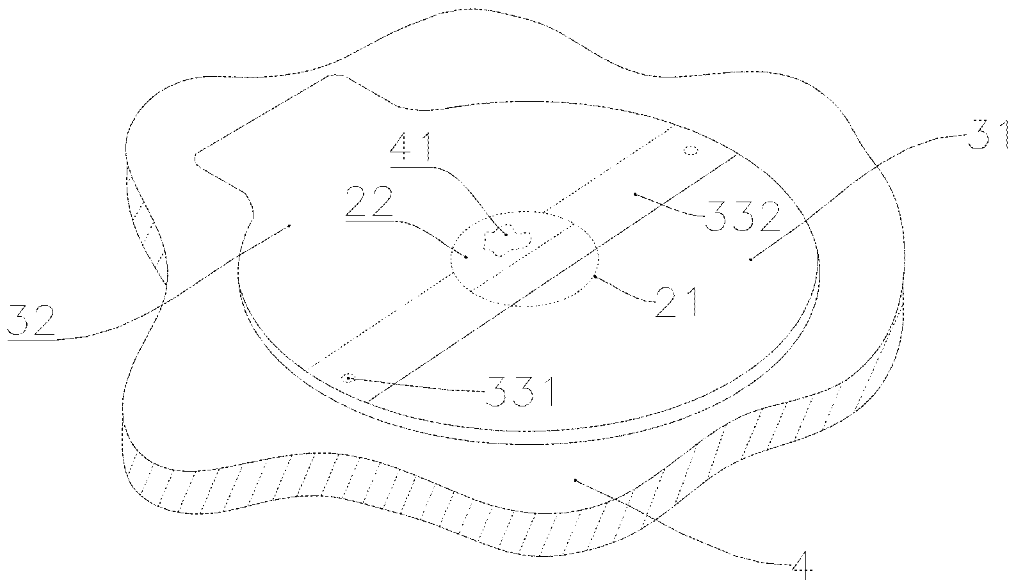

FIG. 15 is schematic diagram V illustrating use of a chest seal according to the present disclosure.

Numerical references: 1-release layer; 2-adhesive layer; 21-exhaust through hole; 22-non-block area; 3-backing layer; 31-lower backing layer; 311-inner periphery; 3111-notch; 312-outer periphery; 313-inner peripheral region; 32-soft backing layer; 323-inner peripheral region; 33-overlapping area; 331-connection area; 332-non-connection area; 333-flow path; 4-chest; 41-wound; 42-effusion.

DETAILED DESCRIPTION OF THE EMBODIMENTS

The present disclosure will now be described in further detail. The embodiments described below are exemplary and are intended to explain the present disclosure, but should not be understood as limiting the present disclosure. Based on the embodiments of the present disclosure, all other embodiments obtained by ordinary technicians in the art without creative work belong to the scope of protection of the present disclosure.

In order to make the above objectives, features, and advantages of the present disclosure more obvious and understandable, specific embodiments of the present disclosure will be described in detail with reference to the drawings below.

In order to solve the problem that the emergency treatment method for open pneumothorax in the existing art is cumbersome to operate and results in unsatisfactory effect, the present disclosure provides a chest seal, as shown in FIGS. 1-15. The chest seal includes: a release layer 1;

an adhesive layer 2, a center of the adhesive layer 2 being opened with an exhaust through hole 21; and a backing layer 3. The adhesive layer 2 is arranged between the release layer 1 and the backing layer 3; the backing layer 3 includes a lower backing layer 31 and a soft backing layer 32;

the lower backing layer 31 and the soft backing layer 32 are staggered and form an overlapping area 33; specifically, the lower backing layer 31 and the soft backing layer 32 overlap at their respective inner peripheral regions 313, 323 to form an elongated overlapping area 33; and the lower backing layer 31 is arranged above the adhesive layer 2 and partially blocks one side of the exhaust through hole 21. A non-block area 22 is formed at another side of the exhaust through hole 21 between the lower backing layer 31 and the exhaust through hole 21, and the soft backing layer 32 completely covers the non-block area 22.

According to the present disclosure, preferably, the soft backing layer 32 is selected from at least one of polyethylene film, polyurethane film, and silicone rubber film; further, the soft backing layer 32 of the present disclosure is preferably a polyurethane film, so that it has good flexibility and biocompatibility, which can improve the patient's comfort and the adaptability of the seal.

According to the present disclosure, preferably, the lower backing layer 31 is selected from at least one of PE film, PET film, OPP film, composite film, glassine paper, coated paper, CCK paper, polyethylene film, polyurethane film, and silicone rubber film; further, considering the flexibility and compliance of the entire seal, according to the present disclosure, preferably, the lower backing layer 31 is selected from at least one of polyethylene film, polyurethane film, and silicone rubber film. Specifically, the lower backing layer 31 in the present disclosure is a polyurethane film.

According to the present disclosure, preferably, the release layer 1 is selected from at least one of PE release film, PET release film, OPP release film, composite release film, glassine release paper, coated release paper, and CCK release paper; further, the release layer 1 of the present disclosure is preferably a PET release film, so that it can provide good release performance and facilitate the peeling and use of the seal.

According to the present disclosure, preferably, the adhesive layer 2 is selected from at least one of silicone gel layer, hydrocolloid layer, and hydrogel layer; further, the adhesive layer 2 of the present disclosure is preferably a hydrogel layer, so that it has good adhesion and biocompatibility, which can ensure that the seal is firmly adhered to the skin while reducing irritation to the skin.

The chest seal provided by the present disclosure utilizes the structural design between the exhaust through hole 21, the lower backing layer 31, and the soft backing layer 32 to prevent external air from entering the chest cavity and discharge the effusion 42 in the chest cavity when a penetrating wound is formed in the chest cavity. Moreover, by adjusting the size of the non-block area 22 between the lower backing layer 31 and the exhaust through hole 21, the drainage efficiency can be accurately controlled. In addition, the chest seal can change an open pneumothorax into a closed pneumothorax, which is simple and quick to operate. It is suitable for emergency treatment of open pneumothorax, reduces the patient's demand for medical resources, and thus saves medical costs to a certain extent.

The traditional circular vent design is not adopted in the present disclosure, but through the staggered arrangement of the lower backing layer 31 and the soft backing layer 32, in which a non-block area 22 is formed between the lower backing layer 31 and the exhaust through hole 21, and the soft backing layer 32 completely covers the non-block area 22. This design not only significantly improves the drainage efficiency, but also can more effectively discharge the effusion 42 in the chest cavity, especially suitable for situations where the wound 41 is large or the effusion 42 is large. Moreover, it also greatly enhances the sealing performance and avoids the risk of air entering the chest cavity and causing tension pneumothorax due to blockage or failure of traditional valve mechanisms.

According to the present disclosure, preferably, the adhesive layer 2 is consistent with the shape of the backing layer 3.

The size design of the non-block area 22 in the present disclosure is not simply to maximize, but is based on a balance between drainage efficiency and sealing. Although an excessively large non-block area can improve the drainage efficiency, it will weaken the sealing performance, increase the risk of external air entering the chest cavity, and may even cause complications such as tension pneumothorax. Therefore, the present disclosure preferably has a cross section of the non-block area 22 that is 1/50~4/5 of the cross section of the exhaust through hole 21.

Further, the present disclosure preferably has a cross-section of the non-block area 22 that is 1/40~1/2 of the cross-section of the exhaust through hole 21 to ensure efficient drainage while maintaining good sealing. Of this size range, the adaptability of different wound sizes and locations are taken into account, while effectively reducing the risk of blockage and complications. A moderate size of the non-block area can avoid fluid accumulation and tissue debris blockage, reduce the possibility of infection caused by the accumulation of effusion 42, and thus provide a more reliable, flexible and targeted solution for emergency treatment of open pneumothorax.

In addition, the lower backing layer 31 and the soft backing layer 32 in the present disclosure are both transparent or translucent. When using the product of the present disclosure, a boundary line between the lower backing layer 31 and the soft backing layer 32 can be used as a product pasting positioning line. When pasting, it is only necessary that the boundary line is above the penetrating wound 41; the complexity of pasting is reduced and the flexibility of use is improved. Moreover, the coverage areas of the penetrating wound 41 and the non-block area 22 can be flexibly adjusted according to actual needs, so as to better adapt to the wound conditions of different patients.

As shown in FIGS. 1-9, at this moment, the lower backing layer 31 is tightly bonded to the adhesive layer 2, and similarly, the soft backing layer 32 excluding the overlapping area 33 with the lower backing layer 31 is also tightly bonded to the adhesive layer 2. Therefore, when in use, the release layer 1 is torn off, and the boundary line between the lower backing layer 31 and the soft backing layer 32 at the exhaust through hole 21 is aligned with the wound 41 (if the wound 41 is small, in order to improve the drainage efficiency, the wound 41 should be located in the non-block area 22 as much as possible), and attached to the chest 4, so that the effusion 42 in the chest cavity can only flow outward through the non-block area 22 in the direction indicated by the flow arrow, and flow out through the overlapping area 33 between the lower backing layer 31 and the soft backing layer 32. And, the soft backing layer 32 can effectively prevent external air from entering the chest cavity.

According to the present disclosure, preferably, the lower backing layer 31 includes an inner periphery 311 and an outer periphery 312; to further improve the drainage efficiency, the inner periphery 311 can be provided with at least one notch 3111, in which the notch 3111 needs to be arranged in the overlapping area 33, and the notch 3111 is connected to the exhaust through hole 21.

Further, in order to prevent the overlapping area 33 of the lower backing layer 31 from being lifted up during exhalation, according to the present disclosure, preferably, the overlapping area 33 includes a connection area 331 and a non-connection area 332, in which an upper part of the exhaust through hole 21 is the non-connection area 332, and the drainage function can also be realized through the non-connection area 332, thereby further improving the drainage efficiency. The non-connection area 332 is located above the exhaust through hole 21 and defines a flow path 333 between the inner peripheral regions 313, 323 of the lower backing layer 31 and the soft backing layer 32; and the soft backing layer 32 is configured to close the flow path 333 to prevent inward airflow and permit outward flow of effusion from the non-block area 22 through the flow path 333.

As shown in FIGS. 10-15, at this moment, the lower backing layer 31 is tightly bonded to the adhesive layer 2, and similarly, the soft backing layer 32 excluding the overlapping area 33 with the lower backing layer 31 is also tightly bonded to the adhesive layer 2. When in use, the release layer 1 is torn off, and the boundary line between the notch 3111 at the exhaust through hole 21 and the soft backing layer 32 is aligned with the wound 41 (if the wound 41 is small, in order to improve the drainage efficiency, the wound 41 should be located in the notch 3111 as much as possible), and attached to the chest 4, so that the effusion 42 in the chest cavity can flow outward through the non-block area 22 and the notch 3111, and flow out through the non-connection area 332 between the lower backing layer 31 and the soft backing layer 32. And, the soft backing layer 32 can effectively prevent external air from entering the chest cavity.

In the present disclosure, the soft backing layer 32 can be fixedly connected to the lower backing layer 31 by adhering, gluing, welding, sewing and buckling; in order to ensure the flexibility and adaptability of bonding, technicians in this field can select the most suitable bonding method according to specific application scenarios. According to the present disclosure, preferably, the soft backing layer 32 is bound to the lower backing layer 31 by gluing.

In order to enhance the connection stability between the lower backing layer 31 and the soft backing layer 32 and improve the drainage efficiency, according to the present disclosure, preferably, the connection area 331 is set at both ends of the overlapping area 33, and the area of the connection area 331 is greater than 0; further, according to the present disclosure, preferably, the connection area 331 is as small as possible, and can be pasted with glue.

According to the present disclosure, preferably, the notch 3111 is an arc-shaped notch whose edge coincides with the edge of the exhaust through hole 21, which can optimize the drainage efficiency while ensuring the overall structural integrity of the seal.

Taking the above ideal embodiment according to the present disclosure as an inspiration, with the above description content, relevant staff can make various changes and modifications within the scope of not deviating from the technical idea of the present disclosure. The technical scope of the present disclosure is not limited to the content in the specification, and its technical scope must be determined according to the scope of claims.

What is claimed is:

1. A chest seal, comprising:

a release layer (1);

an adhesive layer (2), wherein a center of the adhesive layer (2) is opened with an exhaust through hole (21);

a backing layer (3), wherein the adhesive layer (2) is arranged between the release layer (1) and the backing layer (3); the backing layer (3) comprises a lower backing layer (31) and a soft backing layer (32);

the lower backing layer (31) and the soft backing layer (32) overlap at their respective inner peripheral regions (313, 323) to form an elongated overlapping area (33);

the lower backing layer (31) is arranged above the adhesive layer (2) and partially blocks one side of the exhaust through hole (21), a non-block area (22) is formed at another side of the exhaust through hole (21) between the lower backing layer (31) and the exhaust through hole (21), and the soft backing layer (32) completely covers the non-block area (22);

the elongated overlapping area (33) comprises two connection areas (331) disposed at two opposite ends of the elongated overlapping area (33) respectively, and a non-connection area (332) disposed between the two connection areas (331); wherein the non-connection area (332) is located above the exhaust through hole (21) and defines a flow path (333) between the inner peripheral regions (313, 323) of the lower backing layer (31) and the soft backing layer (32); and the soft backing layer (32) is configured to close the flow path (333) to prevent inward airflow and permit outward flow of effusion from the non-block area (22) through the flow path (333);

the lower backing layer (31) comprises an inner periphery (311) and an outer periphery (312); the inner periphery (311) is provided with at least one notch (3111); the notch (3111) is arranged in the elongated overlapping area (33); and the notch (3111) is in fluid communication with the exhaust through hole (21).

2. The chest seal according to claim 1, wherein the adhesive layer (2) is consistent with the shape of the backing layer (3).

3. The chest seal according to claim 1, wherein the cross section of the non-block area (22) is 1/50~4/5 of the cross section of the exhaust through hole (21).

4. The chest seal according to claim 1, wherein the area of each connection area (331) is greater than 0.

5. The chest seal according to claim 1, wherein the notch (3111) is an arc-shaped notch whose edge coincides with an edge of the exhaust through hole (21).

6. The chest seal according to claim 1, wherein the soft backing layer (32) is selected from at least one of polyethylene film, polyurethane film, and silicone rubber film.

7. The chest seal according to claim 1, wherein the release layer (1) is selected from at least one of polyethylene (PE) release film, polyethylene terephthalate (PET) release film, oriented polypropylene (OPP) release film, composite release film, glassine release paper, coated release paper, and clay coated kraft (CCK) release paper.

8. The chest seal according to claim 1, wherein the adhesive layer (2) is selected from at least one of silicone gel layer, hydrocolloid layer, and hydrogel layer.

* * * * *